United States Patent
Wang et al.

(10) Patent No.: US 12,380,811 B2
(45) Date of Patent: Aug. 5, 2025

(54) SYSTEM AND METHOD FOR SIMULATING A RESPIRATORY SYSTEM

(71) Applicants: Yang Wang, Rolla, MO (US); Weixing Hao, Rolla, MO (US); Yue-Wern Huang, Rolla, MO (US)

(72) Inventors: Yang Wang, Rolla, MO (US); Weixing Hao, Rolla, MO (US); Yue-Wern Huang, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 348 days.

(21) Appl. No.: 18/189,488

(22) Filed: Mar. 24, 2023

(65) Prior Publication Data
US 2023/0306874 A1    Sep. 28, 2023

Related U.S. Application Data

(60) Provisional application No. 63/323,698, filed on Mar. 25, 2022.

(51) Int. Cl.
*G01N 33/497* (2006.01)
*G09B 23/30* (2006.01)

(52) U.S. Cl.
CPC .......... *G09B 23/30* (2013.01); *G01N 33/497* (2013.01)

(58) Field of Classification Search
CPC ............................. G09B 23/30; G01N 33/497
See application file for complete search history.

(56) References Cited

U.S. PATENT DOCUMENTS

2016/0217709 A1 *  7/2016  Minskoff ............... G09B 23/30
2021/0172840 A1 *  6/2021  Finlay ................. G01N 1/2205

FOREIGN PATENT DOCUMENTS

WO   WO-2019016094 A1 *  1/2019  ............... A24C 5/34

OTHER PUBLICATIONS

Koehler et al., "Development of a Sampler for Total Aerosol Deposition in the Human Respiratory Tract," Ann. Occup. Hyg., vol. 53, No. 7, pp. 731-738, 2009, 8 pages.

(Continued)

*Primary Examiner* — John E Breene
*Assistant Examiner* — Alex T Devito
(74) *Attorney, Agent, or Firm* — HOVEY WILLIAMS LLP

(57) ABSTRACT

A system and method for simulating a human respiratory system to facilitate investigating the functioning of the respiratory system, such as the generation and effects of secondhand smoke. An aerosol generator, which may include an atomizer, is configured to generate an aerosol. A series of filter media includes, in order, an inhaling extrathoracic filter media, an inhaling tracheobronchial filter media, an alveolar filter media, an exhaling tracheobronchial filter media, and an exhaling extrathoracic filter media. Each filter media includes one or more layers of a material having a fiber diameter and a weight that simulate the corresponding region of the respiratory system. A conduit may be configured to define a path for the aerosol from the aerosol generator through the series of filter media. An instrument, such as a scanning mobility particle sizer, may be used to measure a property of a secondhand aerosol exiting the exhaling extrathoracic filter media.

20 Claims, 5 Drawing Sheets

(56) References Cited

OTHER PUBLICATIONS

Bair, W.J., "The ICRP Human Respiratory Tract Model for Radiological Protection," Radiation Protection Dosimetry, vol. 60, Issue 4, Jul. 1, 1995, pp. 307-310, https://doi.org/10.1093/oxfordjournals.rpd.a082732, 1 page (abstract only attached).
ICRP, 1994. Human Respiratory Tract Model for Radiological Protection. ICRP Publication 66. Ann. ICRP 24 (1-3), 1 page (abstract only attached).
Vitrocell Smoking Machines, Vitrocell Systems GmbH, Waldkirch, Germany, www.vitrocell.com, 6 pages (printed on Jan. 11, 2024).
Cerulean Linear Smoking Machines, 2023, Home Office, Milton Keynes, United Kingdom, www.cerulean.com, 7 pages (printed on Jan. 11, 2024).
Cambustion SCS Smoking Machine, Cambridge, United Kingdom, www.cambustion.com, 6 pages (printed on Jan. 11, 2024).
Hao et al., "A filter-based system mimicking the particle deposition and penetration in human respiratory system for secondhand smoke generation and characterization," Inhalation Toxicology (2022), DOI: 10.1080/08958378.2022.2075493, 12 pages.

\* cited by examiner

110 — Generating an aerosol

114 — Passing the aerosol through a series of filter media, including -
- one or more first filter media simulating an extrathoracic region,
- one or more second filter media simulating a tracheobronchial region, and
- one or more third filter media simulating an alveolar region.

118 — The series of filter media including, in order -
- an inhaling extrathoracic filter media,
- an inhaling tracheobronchial filter media,
- an alveolar filter media,
- an exhaling tracheobronchial filter media, and
- an exhaling extrathoracic filter media.

120 — Measuring a property of a secondary aerosol exiting the series of filter media.

Fig. 6.

SYSTEM AND METHOD FOR SIMULATING A RESPIRATORY SYSTEM

RELATED APPLICATIONS

The present U.S. non-provisional patent application is related to and claims priority benefit of an earlier-filed U.S. provisional patent application titled "Simulated Respiratory System and Method," Ser. No. 63/323,698, filed Mar. 25, 2022. The entire content of the identified earlier-filed application is incorporated by reference as if fully set forth herein.

STATEMENT REGARDING FEDERALLY-SPONSORED RESEARCH OR DEVELOPMENT

This invention was made with Government support under Contract No.: 2034198 awarded by the United States National Science Foundation. The Government has certain rights in the invention.

FIELD

The present invention is related to systems and methods for simulating respiratory systems, and, more particularly, embodiments concern a system and method for simulating a respiratory system including a series of filter media simulating an extrathoracic region, a tracheobronchial region, and an alveolar region of the respiratory system.

BACKGROUND

It is sometimes useful to simulate biological systems, such as respiratory systems, in order to test the functioning of such systems under different conditions. This is particularly true when there is a scarcity of repeatable data from living subjects. Simulated systems are therefore useful in that they can facilitate the identification and study of problems and the development of solutions for maintaining or returning to proper function. Currently, simulated respiratory systems do not achieve sufficiently accurate simulated functioning for some testing purposes.

This background discussion is intended to provide information related to the present invention which is not necessarily prior art.

SUMMARY

Embodiments address the above-described and other problems and limitations by providing a system and method for simulating a respiratory system including a series of filter media simulating an extrathoracic region, tracheobronchial region, and an alveolar region of the respiratory system. The simulated respiratory system may be used, for example, to investigate the effects of aerosols on various regions of the human lung, including simulating secondhand aerosol generation by the human lung.

A first embodiment of a system for simulating a respiratory system may include an aerosol generator, a series of filter media, and a conduit. The aerosol generator may be configured to generate an aerosol. The series of filter media may include one or more first filter media simulating an extrathoracic region of the respiratory system, one or more second filter media simulating a tracheobronchial region of the respiratory system, and one or more third filter media simulating an alveolar region of the respiratory system. The conduit may be configured to define a path for the aerosol from the aerosol generator through the series of filter media.

Various implementations of the above-described first embodiment may include any one or more of the following features. The respiratory system may be a normal human respiratory system. Each first filter media of the one or more first filter media may include between one and three (e.g., two) layers of a first material having a fiber diameter of between one hundred twenty and one hundred thirty micrometers and a weight of between seventy and eighty grams per square meter. Each first filter media of the one or more first filter media may include one or more (e.g., one) layers of a first material having a fiber diameter of between two hundred fifteen and two hundred twenty-five micrometers and a weight of between one hundred fifty-five and one hundred sixty-five grams per square meter.

Each second filter media of the one or more second filter media may include between three and five (e.g., four) layers of a second material having a fiber diameter of between eighty-five and ninety-five micrometers and a weight of between sixty-five and seventy-five grams per square meter. Each second filter media of the one or more second filter media may include between three and five (e.g., four) layers of a second material having a fiber diameter of between one hundred ninety-five and two hundred five micrometers and a weight of between one hundred fifty-five and one hundred sixty-five grams per square meter.

Each third filter media of the one or more third filter media may include between one and three (e.g., two) layers of a third material having a fiber diameter of between two hundred twenty-five and two hundred thirty-five micrometers, and a weight of between one hundred and one hundred ten grams per square meter. Each third filter media of the one or more third filter media may include between three and five (e.g., four) layers of a third material having a fiber diameter of between two hundred five and two hundred fifteen micrometers, and a weight of between one hundred forty and one hundred fifty grams per square meter. Each third filter media of the one or more third filter media may include one or more (e.g., one) layers of a third material having a fiber diameter of between seven-point-five and twelve-point-five micrometers and a weight of between one hundred twenty-five and one hundred thirty-five grams per square meter.

The one or more first filter media may include an inhaling extrathoracic filter media and an exhaling extrathoracic filter media, and the one or more second filter media may include an inhaling tracheobronchial filter media and an exhaling tracheobronchial filter media, and the series of filter media may be arranged, in order, as follows: the inhaling extrathoracic filter media, the inhaling tracheobronchial filter media, the one or more third filter media simulating the alveolar region, the exhaling tracheobronchial filter media, and the exhaling extrathoracic filter media. The system may further include an instrument configured to measure a property of a secondhand aerosol exiting the exhaling extrathoracic filter media.

A second embodiment of a system for simulating a human respiratory system may include an aerosol generator, a series of filter media, a conduit, and an instrument. The aerosol generator may include an atomizer configured to generate an aerosol. The series of filter media may include, in order, an inhaling extrathoracic filter media simulating an inhaling extrathoracic region of the human respiratory system, an inhaling tracheobronchial filter media simulating an inhaling tracheobronchial region of the human respiratory system, an alveolar filter media simulating an alveolar region of the human respiratory system, an exhaling tracheobronchial filter media simulating an exhaling tracheobronchial region of the human respiratory system, and an exhaling extrathoracic filter media simulating an exhaling extrathoracic region of the human respiratory system, wherein a secondhand aerosol may exit the exhaling extrathoracic filter media. The conduit may be configured to define a path for the aerosol from the aerosol generator through the series of filter media. The instrument may be configured to measure a property of the secondhand aerosol exiting the exhaling extrathoracic filter media.

Various implementations of the above-described second embodiment may include any one or more of the following features. Each of the inhaling extrathoracic filter media and the exhaling extrathoracic filter media may include between one and three (e.g., two) layers of a first material having a fiber diameter of between one hundred twenty and one hundred thirty micrometers and a weight of between seventy and eighty grams per square meter. Each of the inhaling extrathoracic filter media and the exhaling extrathoracic filter media may include one or more (e.g., one) layers of a first material having a fiber diameter of between two hundred fifteen and two hundred twenty-five micrometers and a weight of between one hundred fifty-five and one hundred sixty-five grams per square meter.

Each of the inhaling tracheobronchial filter media and exhaling tracheobronchial filter media may include between three and five (e.g., four) layers of a second material having a fiber diameter of between eighty-five and ninety-five micrometers and a weight of between sixty-five and seventy-five grams per square meter. Each of the inhaling tracheobronchial filter media and exhaling tracheobronchial filter media may include between three and five (e.g., four) layers of a second material having a fiber diameter of between one hundred ninety-five and two hundred five micrometers and a weight of between one hundred fifty-five and one hundred sixty-five grams per square meter.

The alveolar filter media may include between one and three (e.g., two) layers of a third material having a fiber diameter of between two hundred twenty-five and two hundred thirty-five micrometers, and a weight of between one hundred and one hundred ten grams per square meter. The alveolar filter media may include between three and five (e.g., four) layers of a third material having a fiber diameter of between two hundred five and two hundred fifteen micrometers, and a weight of between one hundred forty to one hundred fifty grams per square meter. The alveolar filter media may include one or more (e.g., one) layers of a third material having a fiber diameter of between seven-point-five and twelve-point-five micrometers and a weight of between one hundred twenty-five and one hundred thirty-five grams per square meter.

An embodiment of a method for simulating a human respiratory system may include the following steps. An aerosol may be artificially generated. The aerosol may be passed through a series of filter media including, in order, an inhaling extrathoracic filter media artificially simulating an inhaling extrathoracic region of the human respiratory system, an inhaling tracheobronchial filter media artificially simulating an inhaling tracheobronchial region of the human respiratory system, the one or more alveolar filter media artificially simulating an alveolar region of the human respiratory system, an exhaling tracheobronchial filter media artificially simulating an inhaling tracheobronchial region of the human respiratory system, and an exhaling extrathoracic filter media artificially simulating an exhaling extrathoracic region of the human respiratory system, wherein a secondhand aerosol exits the exhaling extrathoracic filter media. A property of the secondhand aerosol exiting the exhaling extrathoracic filter media may be measured.

This summary is not intended to identify essential features of the present invention, and is not intended to be used to limit the scope of the claims. These and other aspects of the present invention are described below in greater detail.

DRAWINGS

Embodiments of the present invention are described in detail below with reference to the attached drawing figures, wherein:

Figures 1, 2:
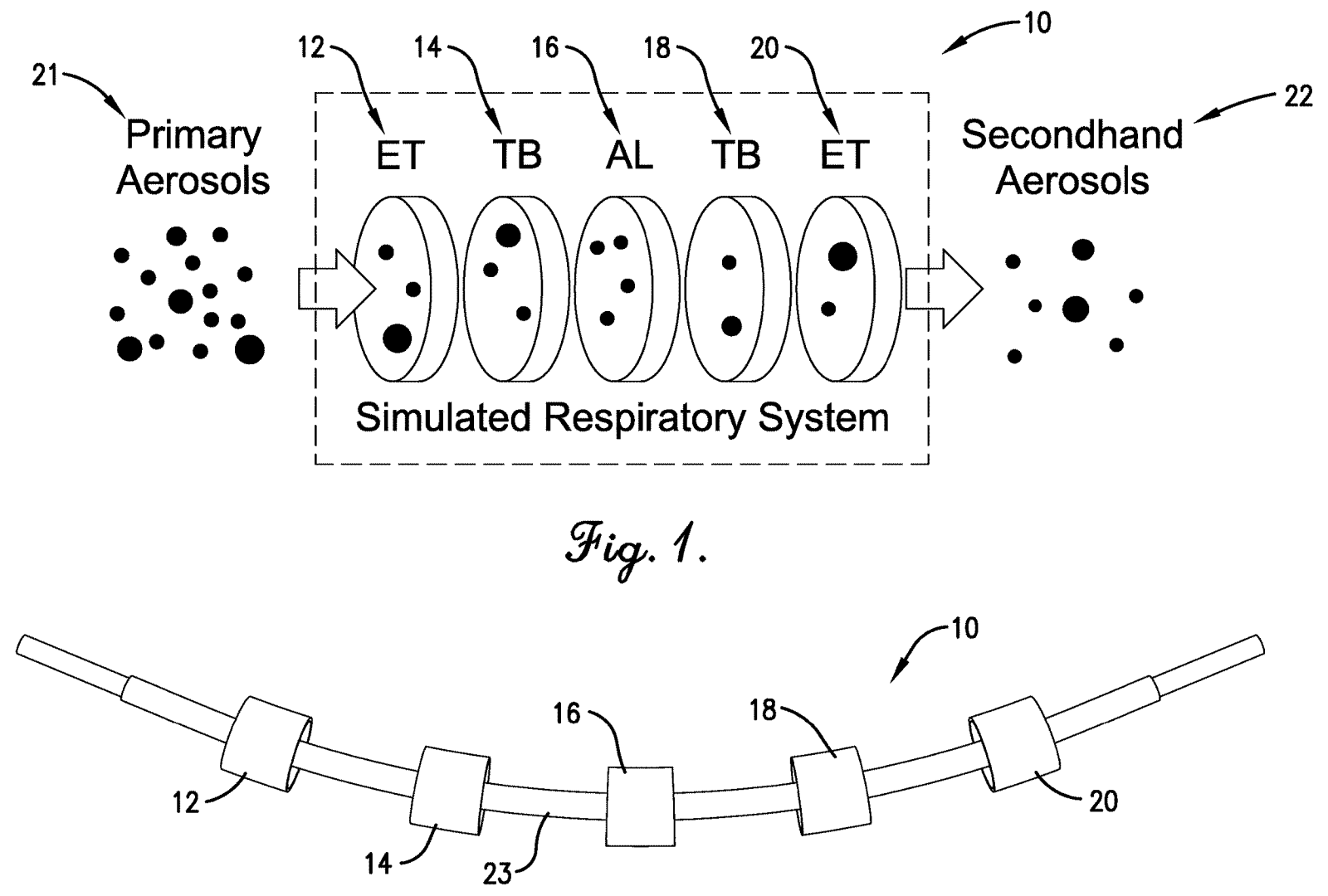

FIG. 1 is a schematic view of an embodiment of a system for simulating a respiratory system;

FIG. 2 is a diagram of the system of FIG. 1;

Figure 3A:
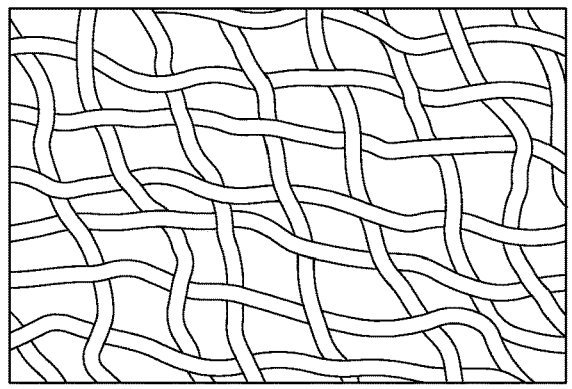
FIG. 3A is a depiction of a first example filter media that could be used in an implementation of the system of FIG. 1.
Figure 3B:
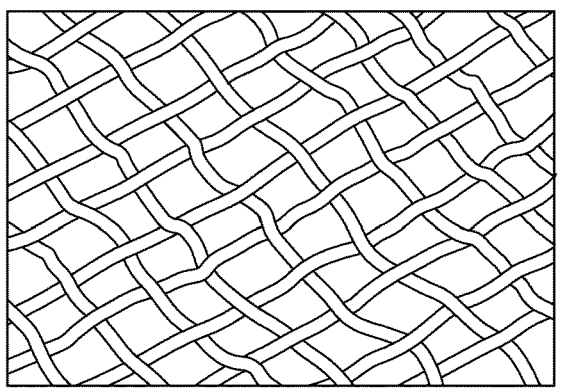
FIG. 3B is a depiction of a second example filter media that could be used in an implementation of the system of FIG. 1.
Figure 3C:
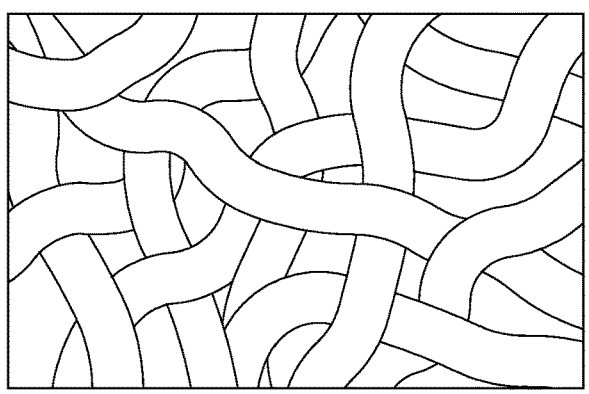
FIG. 3C is a depiction of a third example filter media that could be used in an implementation of the system of FIG. 1.
Figure 4:
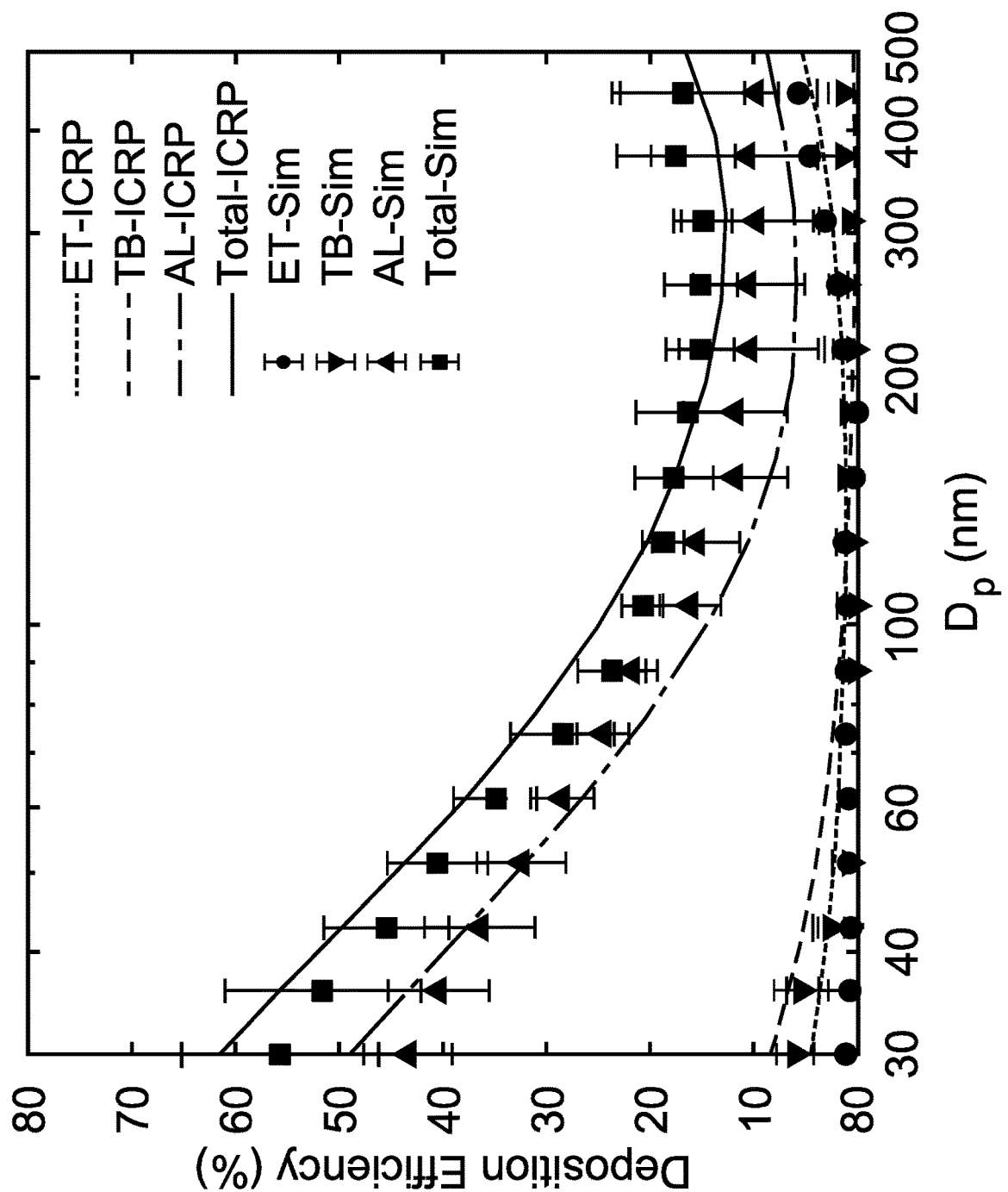
Figure 5:
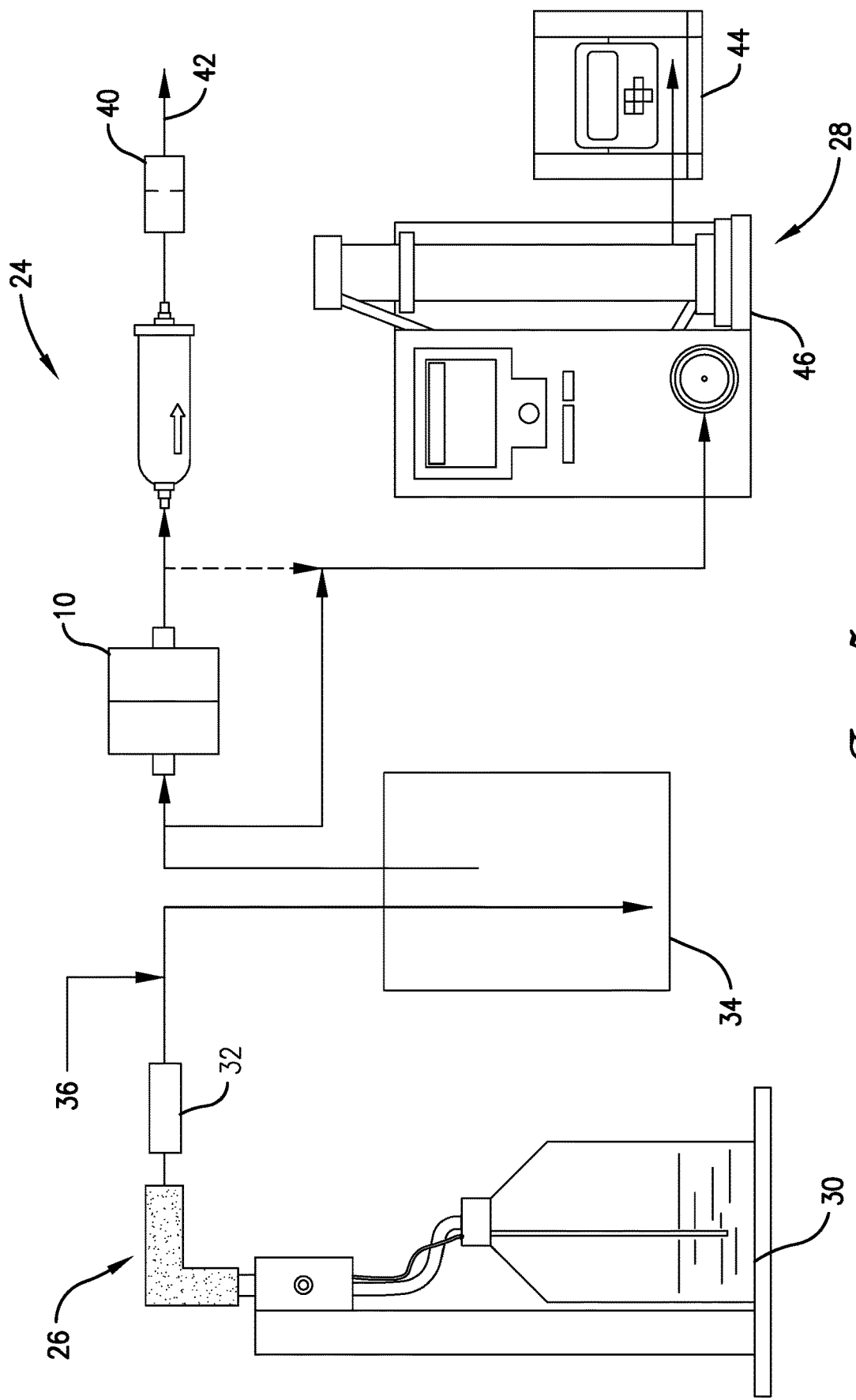

FIG. 4 is a graph showing size-dependent NaCl aerosol deposition efficiencies of specific materials used in the filter medias simulating an extrathoracic region, a tracheobronchial region, and an alveolar region of a human respiratory system, and the entire human respiratory system, and a comparison to the theoretical deposition efficiencies derived from an International Commission on Radiological Protection model;

FIG. 5 is a schematic view of an embodiment of the system of FIG. 1 as part of a larger testing apparatus; and FIG. 6 is a flowchart of an embodiment of a method of simulating a respiratory system.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment," "an embodiment," or "embodiments" mean that the feature or features referred to are included in at least one embodiment of the invention. Separate references to "one embodiment," "an embodiment," or "embodiments" in this description do not necessarily refer to the same embodiment and are not mutually exclusive unless so stated. Specifically, a feature, structure, act, etc. described in one embodiment may also be included in other embodiments, but is not necessarily included. Thus, particular implementations of the present invention can include a variety of combinations and/or integrations of the embodiments described herein.

Broadly, embodiments of the present invention provide a system and method for simulating a respiratory system, including a series of filter media representing an extrathoracic region, a tracheobronchial region, and an alveolar region of the respiratory system. Example applications include investigating the effects of aerosols, such as are associated with electronic cigarettes, on various regions of the human lung, including simulating secondhand aerosol generation by the human lung, without involving human test subjects. In particular, embodiments advantageously simulate the particle deposition in the alveolar region and the creation of secondhand aerosols, and facilitate predicting the toxicological profile associated with respirated secondhand aerosols.

Referring to FIGS. 1-5, an embodiment of a system 10 is shown for simulating a respiratory system, including a series of filter media representing various regions of the respiratory system. The system has use in, for example, facilitating the investigation of the functioning of the respiratory system. Though described herein with regard to simulating a normal human respiratory system, it will be appreciated that embodiments may be adapted, by, e.g., changing the filter media, to simulate abnormal human respiratory systems or the respiratory systems of other organisms.

The system 10 may broadly include one or more first filter media 12, 20 configured to artificially simulate the physical functioning of an extrathoracic (ET) region of the respiratory system, one or more second filter media 14, 18 configured to artificially simulate the physical functioning of a tracheobronchial (TB) region of the respiratory system, and one or more third filter media 16 configured to artificially simulate the physical functioning of an alveolar (AL) region of the respiratory system. Further, each filter media of the series of filter media may include one or more layers of material, as discussed in detail below. In one implementation, to simulate the passage of air flow during regular breathing, an inhaling ET region filter media 12 and an exhaling ET region filter media 20 may simulate the ET region of the respiratory system. An inhaling TB region filter media 14 and an exhaling TB region filter media 18 may simulate the TB region of the respiratory system. An AL region filter media 16 may simulate the AL region of the respiratory system. Thus, in one implementation, the series of filter media may include the following, arranged in order: the inhaling ET region filter media 12, the inhaling TB region filter media 14, the AL region filter media 16, the exhaling TB region filter media 18, and the exhaling ET region filter media 20. In operation, primary aerosols 21 may be introduced into the series of filters (i.e., at the inhaling ET region filter media 12) and secondhand aerosols 22 may exit the series of filters (i.e. at the exhaling ET region filter media 20).

The primary aerosols 21 and secondhand aerosols 22 may differ due to physical processes occurring as the aerosolized gas passes through the filter media, similar to what occurs in a biological respiratory system. For example, primary aerosols 21, such as smoke, contain several smaller smoke particles. As the smoke particles enter the respiratory system, they deposit on epithelial cells through inertial impaction, interception, and Brownian diffusion, each playing a different role in capturing particles of various size ranges. Epithelial cells are those cells that line different surfaces of the human body. For example, epithelial cells are found on skin, blood vessels, the urinary tract, and many organs. Brownian diffusion is a random wiggling motion of small airborne particles in still air, resulting from the impact of surrounding gas molecules. In a lung, this random wiggling motion enables particles to deposit on the lung walls.

Additionally, particles of specific sizes may have different deposition efficiencies in the ET, TB, and AL respiratory airways due to variations in the structure, air flow rate, and particle residence time. As a result of particle deposition in the respiratory system, secondhand aerosols have a smaller number-based size distribution compared to primary aerosols. In one application, the system may be used to generate secondhand aerosol particles derived from electronic cigarettes. In other applications, the secondhand aerosol particles may be derived from regular cigarettes, or from particles existent in ambient air, smog, and/or other incoming primary aerosols.

The size-dependent deposition efficiency is a measurement that is beneficial for determining the ratio of particles deposited in the various areas of the human respiratory systems and respiratory system as a whole to particles not deposited through those various areas and the respiratory system as a whole. To recapitulate the size-dependent deposition efficiency, the International Commission on Radiological Protection (ICRP) has developed a model that describes the deposition efficiencies in different regions of the human respiratory system. Numerical models based on computational fluid dynamics (CFD) have also been developed to examine the particle deposition in the human respiratory system, where the human respiratory tract model is designed to provide semi-empirical deposition efficiency from the oronasal cavities to the pulmonary region. Apart from particle deposition, hygroscopic growth of particles is also considered in the ICRP models. Generally, smoke particle size increases due to hygroscopic growth of particles under high relative humidity (greater than ninety (90) percent) in the respiratory system. The hygroscopic growth of smoke particle size also affects the deposition efficiencies in different regions of the respiratory system.

Generally, a higher flow rate leads to enhanced particle deposition for particles above two hundred (200) nm and reduced particle deposition for particles below fifty (50) nm. The reduced deposition of the smaller particles under a higher flow rate originates from the shortened residence time of particles in the filter media, where the particles have a lower probability of being captured by the filter media. The greater deposition of larger particles under a higher flow rate results from the increased particle inertia and enhanced particle capture by impaction and interception. However, the change of the size-dependent particle deposition is not significant, where the absolute difference of particle deposition efficiency is below twenty (20) percent.

To simulate a human respiratory system, including particle deposition in the various regions of a human respiratory system, the particle deposition efficiency (or the filtration efficiency of particles) through the material used in the series of filter media should satisfy the ICRP model under the humidity relevant to human lung conditions. Assuming that the filtration efficiency of the filter materials used for the ET, TB, and AL regions are $\eta_{f,ET}$, $\eta_{f,TB}$ and $\eta_{f,AL}$, and the particle deposition efficiencies in the ET, TB, and AL regions in the ICRP model are $\eta_{ET}$, $\eta_{TB}$, and $\eta_{AL}$, equations (1)-(3) are used to relate the wholistic deposition efficiencies in ET, TB, and AL regions of a human lung to the respective specific filter deposition efficiencies. The particles deposit on the ET and TB filters both upstream and downstream of the AL filter.

Regarding equations (4)-(7), $\eta_{f,ET}$, $\eta_{f,TB}$, $\eta_{f,AL}$, $\eta_{ET}$ (4), $\eta_{TB}$ (5), and $\eta_{AL}$ (6) are dependent on particle size ($D_p$), where $\eta_{ET}$ (4), $\eta_{TB}$ (5), and $\eta_{AL}$ (6) also satisfy the deposition efficiency and the filtration efficiency of the ICRP model. $D_p$ is in micrometers, and IF (7) is the inhalable fraction. The filtration efficiencies of the filter media ($\eta_{f,ET}$, $\eta_{f,TB}$, and $\eta_{f,AL}$) can be obtained by solving Eqs. (1)-(3) using the non-linear solver in MATLAB®. Filter materials that have filtration efficiencies approximating the values of $\eta_{f,ET}$, $\eta_{f,TB}$, and $\eta_{f,AL}$ are ideal candidates for the simulated respiratory system.

$$\eta_{ET} = \eta_{f,ET} + \eta_{f,ET}(1 - \eta_{f,AL})(1 - \eta_{f,ET})(1 - \eta_{f,TB})^2 \quad (1)$$

$$\eta_{TB} = \eta_{f,TB}(1 - \eta_{f,ET}) + \eta_{f,TB}(1 - \eta_{f,AL})(1 - \eta_{f,ET})(1 - \eta_{f,TB}) \quad (2)$$

$$\eta_{AL} = \eta_{f,AL}(1 - \eta_{f,ET})(1 - \eta_{f,TB}) \quad (3)$$

$$\eta_{ET} = IF\left[\frac{1}{1 + \exp(6.84 + 1.18\ln D_p)} + \frac{1}{1 + \exp(0.924 - 1.86\ln D_p)}\right] \quad (4)$$

$$\eta_{TB} = \frac{0.00352}{D_p}\{\exp[-0.234(\ln D_p + 3.40)^2] + 63.9\exp[-0.819(\ln D_p - 1.61)^2]\} \quad (5)$$

$$\eta_{AL} = \frac{0.0155}{D_p}\{\exp[-0.416(\ln D_p + 2.84)^2] + 19.1\exp[-0.482(\ln D_p - 1.36)^2]\} \quad (6)$$

$$IF = 1 - 0.500\left(\frac{1}{1 + 0.000760 D_p^2}\right) \quad (7)$$

The filter media are arranged as shown in FIGS. 1 and 2 to form the simulated respiratory system. The particle deposition efficiency is determined and compared against the ICRP model, which is calculated using $$\eta_{Tot} = IF\left[0.0587 + \frac{0.991}{1 + \exp(4.77 + 1.49\ln D_p)} + \frac{0.943}{1 + \exp(0.508 - 2.58\ln D_p)}\right] \quad (8)$$

Each filter media may include one or more layers of material. The addition of layers has been taken into consideration when determining such preferred embodiments. In various implementations, different filter materials and different numbers of layers may be used to achieve the desired function. Properties such as filter material, brand, filter material fiber diameter, and filter weight (measured in grams per square meter (GSM) (g/m2)) may be considered in alternative implementations.

FIG. 2 is a block diagram of an embodiment of the system 10. A conduit or tube 23 is disposed between adjacent filters 12, 14, 16, 18, 20 to direct aerosolized airflow through the system 10. The size distribution and mobility size distribution of aerosols may, as desired or required, be tested immediately upstream and immediately downstream of a given filter media using a filtration assessment section 28, as described further below, in order to determine the deposition efficiency of that particular filter media. For example, measuring the size distribution and mobility size distribution of the aerosols contained in the tube 23 immediately before and after the AL region filter 16 would facilitate determining the deposition efficiency of AL region filter 16.

Referring particularly to FIGS. 3A-3C, each filter media may be sealed within a suitable cartridge. For example, disc-shaped filter material may be firmly pressed onto a mesh support and sealed at the edge, defined along the cartridge. The following various properties of embodiments of filter media described herein are preferred, although other possible embodiments may fall within the scope of the present invention. That is to say, other embodiments of filter media that correspond to the deposition efficiencies listed by the ICRP for the TB, ET, and AL regions of a human lung, or other models, as desired or required, are within the scope of the present invention.

FIG. 3A is a depiction of a plurality of fibers of an implementation of the present invention, wherein the inhaling ET region filter media 12 and the exhaling ET region filter media 20 may include between one and three (e.g., two) layers of a silk or silk-like material having a fiber diameter between one hundred twenty (120) and one hundred thirty (130) μm and a GSM between seventy (70) and eighty (80) g/m2. In another implementation, the inhaling ET region filter 12 and the exhaling ET region filter 20 may include one or more (e.g., one) layers of a flannel or flannel-like material having a fiber diameter between two hundred fifteen (215) and two hundred twenty-five (225) μm and a GSM between one hundred fifty-five (155) and one hundred sixty-five (165) g/m2.

FIG. 3B is a depiction of a plurality of fibers of an implementation of the present invention, wherein the inhaling TB region filter media 14 and the exhaling TB region filter media 18 may include between three and five (e.g., four) layers of a silk or silk-like material having a fiber diameter between eighty-five (85) and ninety-five (95) μm and a GSM between sixty-five (65) and seventy-five (75) g/m2. In another implementation, the inhaling TB region filter media 14 and the exhaling TB region filter media 20 may include between three and five (e.g., four) layers of a polyester woven chiffon or polyester woven chiffon-like material having a fiber diameter between one hundred ninety-five (195) and two hundred five (205) μm and a GSM between one hundred fifty-five (155) and one hundred sixty-five (165) g/m2.

FIG. 3C is a depiction of a photograph of a plurality of fibers of an implementation of the present invention, wherein the AL region filter media 16 may include between one and three (e.g., two) layers of a polyester or polyester-like material having a fiber diameter between two hundred twenty-five (225) and two hundred thirty-five (235) μm and a GSM between one hundred (100) and one hundred ten (110) g/m2. In another implementation, the AL region filter media 16 may include between three and five (e.g., four) layers of a cotton or cotton-like material having a fiber diameter between two hundred five (205) and two hundred fifteen (215) μm and a GSM between one hundred forty (140) and one hundred fifty (150) g/m2. In another implementation, the AL region filter media 16 may include one or more (e.g., one) layers of a bamboo cloth or bamboo cloth-like material having a fiber diameter between seven-point-five (7.5) and twelve-point-five (12.5) μm and a GSM between one hundred twenty-five (125) and one hundred thirty-five (135) g/m2.

Referring particularly to FIG. 4, a graph 50 is shown of size-dependent NaCl aerosol deposition efficiencies of specific fabric materials simulating the ET region (ET-Sim), the TB region (TB-Sim), and the AL region (AL-Sim), and the entire human respiratory system (Total-Sim), and a comparison to the corresponding theoretical deposition efficiencies (ET-ICRP, TB-ICRP, AL-ICRP, Total-ICRP) derived from the ICRP model. In particular, two layers of Thai silk type A (fiber diameter one hundred twenty-five (125) μm, GSM seventy-six-point-zero-five (76.05) g/m2), four layers of Thai silk type B (fiber diameter ninety (90) μm, GSM seventy-two-point-zero-nine (72.09) g/m2), and two layers of knit polyester (fiber diameter two hundred thirty (230) μm, GSM one hundred five-point-four-four (105.44) g/m2) have filtration efficiencies similar to those of the ET, TB, and AL regions ($\eta_{f,ET}$, $\eta_{f,TB}$, and $\eta_{f,AL}$), respectively, under a relative humidity of ninety (90) percent, which are derived from the ICRP model. FIG. 4 shows higher particle deposition efficiency for particles below fifty (50) nm (greater than forty (40) percent), and enhanced deposition efficiencies for particles above three hundred nm, which result from particle capture in the simulated AL and ET regions. On average, the absolute difference of aerosol deposition efficiencies between the simulated respiratory system and the ICRP model was below ten (10) percent in the size range of thirty (30) to five hundred (500) nm. Collectively, such a system can be used to simulate particle deposition in the human respiratory system and the production of secondhand aerosols.

Referring particularly to FIG. 5, the system 10 may further include a testing apparatus 24. The testing apparatus 24 may include an aerosol generation section 26 and a filtration assessment section 28. In one implementation, the aerosol generation section 26 may include a constant output atomizer 30 nebulizing a NaCl-water solution with a mass concentration of 0.1%. The atomizer 30 may generate aerosols at a flow rate of three (3.0) liters per minute (lpm). The aerosols may then be diluted by an inline diluter 32. Subsequently, the aerosols, together with a stream of humidified and filtered make-up air 36, may be introduced to a mixing chamber 34. To control the relative humidity of the makeup air 36 and hence the relative humidity of the mixed aerosol flow, the make-up air 36 may be introduced into a fritted glass water bubbler, the temperature of which is controlled by heating tape.

In one implementation, the relative humidity of the mixed aerosol flow may be determined by the temperature of the water bubbler and measured by a relative humidity sensor. The relative humidity of the mixed aerosol flow may be maintained at ninety (90) percent plus-or-minus five (5) percent, which simulates the lung environment to induce the hygroscopic growth of the aerosols. The homogeneous aerosols may be directed into the simulated respiratory system 10. The flow rate of the mixed aerosol through the system 10 may be maintained at six (6) lpm using a critical orifice 40 installed between the system 10 and a vacuum 42.

In one implementation, the filtration assessment section 28 may include a scanning mobility particle sizer 46. The sizer 46 may measure the mobility size distributions of aerosols upstream and downstream of the system 10, and may measure the mobility size distributions of aerosols upstream and downstream of the different filter medias. For example, the scanning mobility particle sizer 46 may measure the mobility size distributions of aerosols upstream and downstream of the inhaling ET region filter media 12 and the inhaling TB region filter media 14. In another example, the scanning mobility particle sizer 46 may measure the mobility size distributions of aerosols upstream and downstream of the inhaling ET region filter media 12 and the AL region filter media 16.

In one implementation, the size distribution of aerosols $(n(D_p))$ may be obtained by scanning the voltage that is applied to a differential mobility analyzer 44. Like the scanning mobility particle sizer 46, the differential mobility analyzer 44 may also determine the size distribution of aerosols $(n(D_p))$ between the various regions filter media 12, 14, 16, 18, 20.

The size-dependent filtration efficiency $(\eta(D_p))$ may be calculated by Eq. (9):

$$\eta(D_p) = 1 - \frac{n_o(D_p)}{n_i(D_p)} \quad (9)$$

where $n_o(D_p)$ and $n_i(D_p)$ are the particle number concentrations for each particle size measured at the outlet (downstream) and inlet (upstream) of the series of filter media. Size-dependent particle number concentrations may be measured multiple (e.g., three (3)) times, and the standard deviation (σ) of the filtration efficiency may be calculated by Eq. (10):

$$\sigma = \frac{n_o(D_p)}{n_i(D_p)} \sqrt{\left(\frac{\sigma_o}{n_o(D_p)}\right)^2 + \left(\frac{\sigma_i}{n_i(D_p)}\right)^2} \quad (10)$$

where $\sigma_o$ and $\sigma_i$ are the standard deviations of the size distributions upstream and downstream of the filter media.

Components of the system 10 may be manufactured from metal, plastic, glass, ceramic, or some other material, including combinations thereof, having desirable properties. The selection of materials may be based on a variety of factors, such as manufacturing method, cost, ability to be cleaned and/or sterilized, and/or other relevant factor(s). Some implementations may include seals between mating components configured to minimize pressure/air leaks. The shapes and dimensions of the seals may be appropriately configured as desired or required.

Referring also to FIG. 6, an embodiment of a method 110 is shown for simulating a respiratory system, such as a normal human respiratory system. The method 110 has use in, for example, facilitating the investigation of the functioning of the respiratory system. Some or all of the method steps may be implemented using components of the system 10 described above, and, similarly, the operation of some or all of the system components may be reflected in the steps of the method 110.

An aerosol may be artificially generated, as shown in 112. Details of the aerosol and its generation may be as described in detail above. The aerosol may be passed through a series of filter media, as shown in 114. Details of passing the aerosol and of the series of filter media, including possible fiber diameters and weights, may be as described in detail above. In particular, as shown in 116, the series of filter media may include one or more first filter media artificially simulating an extrathoracic region of the respiratory system, one or more second filter media artificially simulating a tracheobronchial region of the respiratory system, and one or more third filter media artificially simulating an alveolar region of the respiratory system.

In one implementation, as shown in 118, the series of filter media may include, in order, an inhaling ET filter media simulating an inhaling extrathoracic region of the human respiratory system, an inhaling TB filter media simulating an inhaling tracheobronchial region, an AL filter media simulating an alveolar region, an exhaling tracheobronchial filter media simulating an exhaling tracheobronchial region, and an exhaling extrathoracic filter media simulating an exhaling extrathoracic region, wherein a secondhand aerosol exits the exhaling ET filter media. A property of the secondhand aerosol exiting the series of filter media may be measured and analyzed, as shown in 120. Details of assessing the secondhand aerosol may be as described in detail above Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be pro- tected by Letters Patent includes the following:

1. A system for simulating a respiratory system, the system comprising:
an aerosol generator generating an aerosol;
a series of filter media including—
one or more first filter media simulating an extrathoracic region of the respiratory system,
one or more second filter media simulating a tracheobronchial region of the respiratory system, and
one or more third filter media simulating an alveolar region of the respiratory system; and
a conduit defining a path for the aerosol from the aerosol generator through the series of filter media.

2. The system of claim 1, wherein the respiratory system is a normal human respiratory system.

3. The system of claim 1, wherein each first filter media of the one or more first filter media includes between one and three layers of a first material having a fiber diameter of between one hundred twenty and one hundred thirty micrometers and a weight of between seventy and eighty grams per square meter.

4. The system of claim 1, wherein each first filter media of the one or more first filter media includes one or more layers of a first material having a fiber diameter of between two hundred fifteen and two hundred twenty-five micrometers and a weight of between one hundred fifty-five and one hundred sixty-five grams per square meter.

5. The system of claim 1, wherein each second filter media of the one or more second filter media includes between three and five layers of a second material having a fiber diameter of between eighty-five and ninety-five micrometers and a weight of between sixty-five and seventy-five grams per square meter.

6. The system of claim 1, wherein each second filter media of the one or more second filter media includes between three and five layers of a second material having a fiber diameter of between one hundred ninety-five and two hundred five micrometers and a weight of between one hundred fifty-five and one hundred sixty-five grams per square meter.

7. The system of claim 1, wherein each third filter media of the one or more third filter media includes between one and three layers of a third material having a fiber diameter of between two hundred twenty-five and two hundred thirty-five micrometers, and a weight of between one hundred and one hundred ten grams per square meter.

8. The system of claim 1, wherein each third filter media of the one or more third filter media includes between three and five layers of a third material having a fiber diameter of between two hundred five and two hundred fifteen micrometers, and a weight of between one hundred forty and one hundred fifty grams per square meter.

9. The system of claim 1, wherein each third filter media of the one or more third filter media includes one or more layers of a third material having a fiber diameter of between seven-point-five and twelve-point-five micrometers and a weight of between one hundred twenty-five and one hundred thirty-five grams per square meter.

10. The system of claim 1, wherein—
the one or more first filter media include an inhaling extrathoracic filter media and an exhaling extrathoracic filter media; and
the one or more second filter media include an inhaling tracheobronchial filter media and an exhaling tracheobronchial filter media,
wherein the series of filter media are arranged, in order, as follows—
the inhaling extrathoracic filter media,
the inhaling tracheobronchial filter media,
the one or more third filter media simulating the alveolar region,
the exhaling tracheobronchial filter media, and
the exhaling extrathoracic filter media.

11. The system of claim 10, further including an instrument measuring a property of a secondhand aerosol exiting the exhaling extrathoracic filter media.

12. A system for simulating a human respiratory system, the system comprising:
an aerosol generator including an atomizer generating aerosol;
a series of filter media including, in order—
an inhaling extrathoracic filter media simulating an inhaling extrathoracic region of the human respiratory system,
an inhaling tracheobronchial filter media simulating an inhaling tracheobronchial region of the human respiratory system,
an alveolar filter media simulating an alveolar region of the human respiratory system,
an exhaling tracheobronchial filter media simulating an exhaling tracheobronchial region of the human respiratory system, and
an exhaling extrathoracic filter media simulating an exhaling extrathoracic region of the human respiratory system;
a conduit defining a path for the aerosol from the aerosol generator through the series of filter media; and
an instrument measuring a property of a secondhand aerosol exiting the exhaling extrathoracic filter media.

13. The system of claim 12, wherein each of the inhaling extrathoracic filter media and the exhaling extrathoracic filter media includes two layers of a first material having a fiber diameter of between one hundred twenty and one hundred thirty micrometers and a weight of between seventy and eighty grams per square meter.

14. The system of claim 12, wherein each of the inhaling extrathoracic filter media and the exhaling extrathoracic filter media includes one layer of a first material having a fiber diameter of between two hundred fifteen and two hundred twenty-five micrometers and a weight of between one hundred fifty-five and one hundred sixty-five grams per square meter.

15. The system of claim 12, wherein each of the inhaling tracheobronchial filter media and exhaling tracheobronchial filter media includes four layers of a second material having a fiber diameter of between eighty-five and ninety-five micrometers and a weight of between sixty-five and seventy-five grams per square meter.

16. The system of claim 12, wherein each of the inhaling tracheobronchial filter media and exhaling tracheobronchial filter media includes four layers of a second material having a fiber diameter of between one hundred ninety-five and two hundred five micrometers and a weight of between one hundred fifty-five and one hundred sixty-five grams per square meter.

17. The system of claim 12, wherein the alveolar filter media includes two layers of a third material having a fiber diameter of between two hundred twenty-five and two hundred thirty-five micrometers, and a weight of between one hundred and one hundred ten grams per square meter.

18. The system of claim 12, wherein the alveolar filter media includes four layers of a third material having a fiber diameter of between two hundred five and two hundred fifteen micrometers, and a weight of between one hundred forty and one hundred fifty grams per square meter.

19. The system of claim 12, wherein the alveolar filter media includes one layer of a third material having a fiber diameter of between seven-point-five and twelve-point-five micrometers and a weight of between one hundred twenty-five and one hundred thirty-five grams per square meter.

20. A method of simulating a human respiratory system, the system comprising:
   artificially generating an aerosol;
   passing the aerosol through a series of filter media, the series of filter media including, in order—
      an inhaling extrathoracic filter media artificially simulating an inhaling extrathoracic region of the human respiratory system,
      an inhaling tracheobronchial filter media artificially simulating an inhaling tracheobronchial region of the human respiratory system,
      the one or more alveolar filter media artificially simulating an alveolar region of the human respiratory system,
      an exhaling tracheobronchial filter media artificially simulating an inhaling tracheobronchial region of the human respiratory system, and
      an exhaling extrathoracic filter media artificially simulating an exhaling extrathoracic region of the human respiratory system,
      wherein a secondhand aerosol exits the exhaling extrathoracic filter media; and
   measuring a property of the secondhand aerosol exiting the exhaling extrathoracic filter media.

* * * * *